United States Patent [19]
Müller et al.

[11] Patent Number: 5,565,561
[45] Date of Patent: Oct. 15, 1996

[54] NATURAL SUBSTANCE CYCLAMENOL AND CHEMICAL DERIVATIVES

[75] Inventors: Hartwig Müller, Velbert; Erwin Bischoff, Wuppertal; Volker-Bernd Fiedler, Leverkusen; Karlheinz Weber, Wuppertal; Burkhard Fugmann, Ratingen; Bruno Rosen, Wülfrath, all of Germany

[73] Assignee: Bayer Aktiengesellschaft, Leverkusen, Germany

[21] Appl. No.: 397,208
[22] PCT Filed: Sep. 13, 1993
[86] PCT No.: PCT/EP93/02472
  § 371 Date: Apr. 27, 1995
  § 102(e) Date: Apr. 27, 1995
[87] PCT Pub. No.: WO94/06774
  PCT Pub. Date: Mar. 31, 1994

[30] Foreign Application Priority Data

Sep. 18, 1992 [DE] Germany ............ 42 31 289.2

[51] Int. Cl.⁶ ............ C07D 225/02; A61K 31/395; C12P 17/10
[52] U.S. Cl. ............ 540/451; 540/452; 540/463; 435/121
[58] Field of Search ............ 540/451, 452, 540/463; 435/121

[56] References Cited

PUBLICATIONS

Biochim. Biophys. Acta 577, Seite 324, (1975).
C. S. Cummins and H. Harris, J. Gen. Microbiol. 15, Seiten 9–10, (1956).
R. M. Kroppenstedt, Chemical Methods in Bacterial Systematics, Seiten 173–199, (1985).
E. B. Shirling and D. Gottlieb, Int. Journal Syst. Bact. 16, Seiten 313–340, (1966).
S. T. Williams and T. Cross, (1971), Actinomycetes, Methods in Microbiology, 4, Seiten 295–334.
D. English and B. R. Andersen, Journal of Immunological Methods 5, (1974), Seiten 249–252.
Duling, MVR 5, Seiten 423–429, 1973.
N. Onishi et al.; A macrocyclic antibiotic M–230–B produced by myxococcus xanthus isolation and characterization, Journal of The Journal of Antibiotics, vol. 37, No. 1, Seiten 13–19. (Jan. 1984).

*Primary Examiner*—Robert T. Bond
*Attorney, Agent, or Firm*—Sprung Horn Kramer & Woods

[57] ABSTRACT

The invention relates to the natural substance cyclamenol of the formula

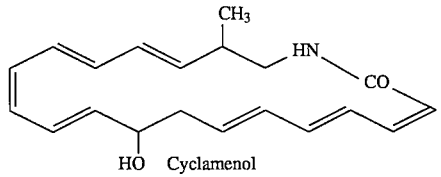

a process for its preparation from microorganisms of the order of the Actinomycetales, in particular from the Streptomyces strain MHW 846, chemical derivatives thereof, and its use as a medicament, in particular for acute and chronic inflammatory disorders in human and veterinary medicine.

4 Claims, 3 Drawing Sheets

NATURAL SUBSTANCE CYCLAMENOL AND CHEMICAL DERIVATIVES

The invention relates to the new natural substance cyclamenol, a process for its preparation from microorganisms of the order of the Actinomycetales, in particular from the Streptomyces strain MHW 846, chemical derivatives, and their use as medicaments, in particular for acute and chronic inflammatory disorders in human and veterinary medicine.

It is already known that a number of microbially produced macrocyclic lactams, such as, for example, hitachimycin, virginiamycin or myxovirescin have an antibacterial or antitumour action [cf. e.g. J. Antibiotics 34, 261 1981), 37; 13 (1984); Biochim. Biophys. Acta 577, 324 (1975)].

The present invention relates to compounds of the general formula (I)

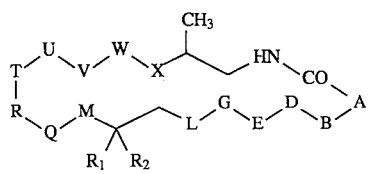

in which

A, B, D, E, G, L, M, Q, R, T, U, V, W and X in each case represent the >CH$_2$ group and R$^1$ and R$^2$ represent hydrogen or R$^1$ represents hydrogen and R$^2$ represents hydroxyl, or R$^1$ and R$^2$ together form the =O group, or A and B, D and E, G and L, M and Q, R and T, U and V and W and X in each case represent the —CH=CH— group, R$^1$ represents hydrogen and R$^2$ represents hydroxyl (cyclamenol) or represents the group of the formula —O—CO—CH$_3$ or —O—Si(CH$_3$)$_3$, Surprisingly, both the new natural substance cyclamenol and its chemical derivatives are distinguished by a strong inhibitory action on central reactions in acute and chronic inflammatory processes.

Processes for the preparation of the compounds of the general formula (I) according to the invention have additionally been found, the production of the natural substance cyclamenol of the formula (Ia)

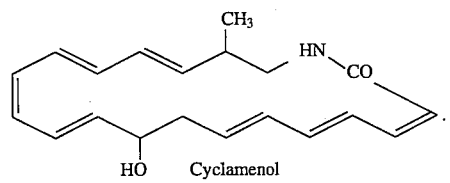

initially being described.

The compound of the general formula (Ia) is produced by culturing the strain Streptomyces spec. MHW 846 in a nutrient medium and then isolating it therefrom.

The compound of the general formula (Ia) according to the invention is produced by the culture of a Streptomyces strain in suitable nutrient solutions under suitable physiological conditions. It is separated off from the culture solution by extraction or by absorption and concentrated by further suitable methods.

The present invention additionally relates to microorganisms of the family Streptomycetaceae which, during culture in a nutrient medium containing carbon and nitrogen sources and also mineral salts, produce a compound which has the properties and parameters shown in the substance characterization in the following under (1) to (6).

The strain Streptomyces spec. HMW 846 from the order of the Actinomycetales, family Streptomycetaceae, genus Streptomyces or variants and mutants derived from it are particularly important for the preparation process. The strain was isolated from a soil sample from Wahuya, Miyagi in Japan. A culture of this strain was deposited in the German Collection of Microorganisms in Brunswick on 14.12.88 under the number DSM 4950.

On the basis of the chemotaxonomic investigations on DL-DAP by C. S. Cummins and H. Harris, J. Gen. Microbiol. 15, 9–10, 1956 and on iso/antiiso fatty acid pattern by R. M. Kroppenstedt in Chemical Methods in Bacterial Systematics (eds. Goodfellow, M.; Minnikin, O. E.) 173–199, 1985, the strain was assigned to the genus Streptomyces. It is a Streptomyces which only poorly forms aerial mycelium on the media according to E. B. Shirling and D. Gottlieb, Int. Journal Syst. Bact. 16, 313–340, 1966, so that the aerial mycelium colour is not clearly ascertainable.

Streptomyces spec. MHW 846 forms melanoid pigment on peptone-iron agar and trypsin agar. Of the C sources supplied, only D-glucose is clearly utilized (Tab. 1). The strain grows in a temperature range from +20° C. to 35° C. At +5° C. and +45° C. no growth is to be observed.

TABLE 1

| C sources utilization of the strain Streptomyces spec. MHW 846 DSM 4950 | |
|---|---|
| Utilization of | Result: |
| L-Arabinose | − |
| Sucrose | − |
| D-Xylose | − |
| Inositol | − |
| D-Mannitol | − |
| D-Fructose | − |
| Rhamnose | − |
| Raffinose | − |
| Cellulose | − |
| D-Glucose | + |

+ = Utilization
− = No utilization

The concentration and isolation of the strain was carried out by the customary methods of Actinomycetes isolation by plating out soil samples suspensions on Petri dishes, four to six weeks' incubation and repeated subculture of individual colonies [Williams, S. T. and Cross, T. (1971), Actinomycetes, in: Methods in Microbiology 4, 295–334, Booth, C. (editor), London—New York: Academic Press].

It has furthermore been found that the compound (Ia) according to the invention is obtained when suitable microorganisms of the family Streptomycetaceae are cultured under aerobic conditions in a nutrient medium which contains assimilable carbon and nitrogen sources and also mineral salts and the compound is isolated by customary methods.

For the process for the preparation of the compound (Ia) according to the invention, nutrient media which contain the customary carbon and nitrogen sources and the necessary salts are used. Carbon sources which can be used are: carbohydrates, in particular polysaccharides, such as e.g. starch, monosaccharides, such as e.g. glucose. Naturally occurring mixtures, such as e.g. malt extract, as well as mixtures of the components mentioned can furthermore be used.

N sources which can be used are the customary nitrogen-containing nutrient media constituents, that is e.g. amino acids, proteins, protein hydrolysates, ammonium salts, naturally occurring complex substances, such as soya-bean flour, milk powder and suitable mixtures thereof.

Auxiliaries required in the nutrient medium are mineral salts, e.g. phosphates, sulphates or chlorides of potassium, of sodium, of calcium, or of magnesium, iron, zinc and manganese. The concentration of these substances can vary within wide limits, in some cases the necessary concentrations of the mineral salts are contained as impurities in the abovementioned carbon or nitrogen sources or in the water used.

All sorts of antifoams such as e.g. polyols or silicones, can furthermore additionally be used as auxiliaries.

The process for the preparation of the compound (Ia) according to the invention can be carried out with the aid of customary solid, semi-solid or liquid nutrient media. Aqueous liquid nutrient media are preferred.

The inoculation of the nutrient media is carried out here by generally customary methods, e.g. by means of slanting tubes or flask cultures.

Culture takes place under aerobic conditions and can be carried out according to the generally customary methods, such as using shaking cultures, e.g. shaking flasks, air-agitated cultures or submerse cultures. Culture preferably takes place in aerobic submerse processes in aerated fermenters, e.g. in customary submerse fermentation tanks. It is possible to carry out culture continuously or batchwise. It is preferably carried out batchwise.

The preparation process is carried out under aerobic conditions; culture can be carried out according to customary methods, that is e.g. using shaking cultures or aerated fermenter cultures. The percentage ratios of the nutrient solution constituents can vary within wide ranges, in general the carbon sources constitute 0.5 to 8%, preferably 0.6 to 6%, the nitrogen sources 0.1 to 5%, preferably 0.5 to 2%, and the salts are present in customary concentrations, preferably in the range between 0.001 and 0.5% by weight. The antifoams are present in a concentration of up to 0.5% strength. The temperatures used for sterilization are around +100° to +140° C., preferably around +120° to +130° C.:

The pH of the growing culture should preferably be kept between about 6 and about 8.5, in particular between 6.5 and 8.0. Too great ape decrease in the acidic range can be avoided by additions of an organic or inorganic base, preferably of $CaCO_3$. As is customary in fermentation technology, automatic pH regulation can also be carried out, in which sterile organic or inorganic acids, e.g. $H_2SO_4$, or sterile alkalis, e.g. NaOH, are sprayed into the culture solution at intervals.

It is expedient to ensure that the microorganisms are adequately brought into contact with oxygen and nutrients. This can be carried out by the generally customary methods such as shaking and stirring.

The culture temperature can be between about +16° C. and +42° C., preferably between +24° C. and +32° C. particularly preferably it is round about +28° C. The duration of culture can be greatly varied, the composition of the nutrient medium and the culture temperature, for example, being important. The particular optimum conditions can be easily determined by any person skilled in the art in the microbial field.

It has emerged that the amount of the compound according to the invention concentrating in the culture broth in general reaches its maximum about 1 to 7, preferably 1 to 4, days after the start of culture.

As general in microbiological processes, cross-infections of the culture media should be avoided. To this end, the customary precaution are taken, such as sterilization of the nutrient media, of the culture vessels and also of the air necessary for aeration. To sterilize the apparatus steam or dry sterilization, for example, can be used.

If foam is formed in an undesired amount during culture, the customary chemical foam depressants, e.g. liquid fats and oils, oil/water emulsions, paraffins, higher alcohols, such as octadecanol, silicone oils, and polyoxyethylene or polyoxypropylene compounds can be added. Foam can also be suppressed or eliminated with the aid of the customary mechanical appliances (which use e.g. centrifugal forces).

The new compound (Ia) is to be found both in the culture supernatant and in the mycelium and can be isolated from the fermentation mixture with the aid of customary extraction and/or chromatography processes and optionally purified. Chromatography can be carried out in the form of column chromatography. High pressure liquid chromatography (HPLC) can be successfully employed. Absorbents which can be employed are the customary inorganic or organic adsorbents, such as e.g. silica gel, magnesium silicate, activated carbon, cellulose, cellulose derivatives, synthetic resins such as polyamides, e.g. acetylated polyamide, dextran gels or modified dextran gels. The eluents used can be all sorts of solvents or solvent mixtures in which the compound according to the invention is soluble. Ethyl acetate, chloroform and methanol or their mixtures (for example mixtures of chloroform and methanol or of ethyl acetate and chloroform) are preferably employed.

Chromatography processes are preferably used for the isolation of the compound (Ia) according to the invention, e.g. non-specific adsorption on sorbents such as silica gel, or gel diffusion chromatography. These are the methods known from the purification of poorly water-soluble natural substances.

The compound (Ia) according to the invention can be obtained from its solutions by the customary methods, e.g. evaporation of the solvent, freeze drying, etc.

In a preferred embodiment, the mycelium is separated from the culture broth, preferably by centrifugation, and extracted several times, preferably twice, with a less polar solvent. Solvents used can be $C_1$–$C_4$-alcohols, $C_1$–$C_4$-ketones or halogenated hydrocarbons. The aqueous organic solution is concentrated in vacuo, e.g. to about 1/20 of the volume of the culture broth, and processed further. The culture broth is extracted several times after separation of the mycelium with a water-immiscible solvent, preferably ethyl acetate, and after concentration further processed to about 1/10 of the starting volume.

The compound (Ia) according to the invention can be isolated from these two crude extracts by customary chromatographic methods, preferably chromatography on silica gel.

It can additionally be bound to non-specific adsorber resins based on polystyrene (e.g. Amberlite XAD from Roehm and Haas or Lewapol CA 9221 from Bayer). Desorption is carried out fractionally, by means of mixtures of water and the abovementioned organic solvents, in particular water/methanol. The active fractions ascertained by test are concentrated at +30° C. to +35° C. under reduced pressure, until the organic solvent is completely removed, and freeze-dried.

The lyophilizate is suspended in water again and preferably extracted with ethyl acetate or other water-immiscible solvents. The compound according to the invention is recovered from the extract by customary chromatographic methods, preferably chromatography on silica gel.

BRIEF DESCRIPTION OF THE DRAWINGS

The drawings are spectra of the new compound. The spectra are more fully described later in the specification.

The compound (Ia) according to the invention is characterized by the following properties:

1) The natural substance is a colourless to pale yellow solid. It sinters on heating and decomposes at greater than >150° C. The optical rotation immediately after dissolving is $[\alpha_{589}^{20}=+3840°$ (c=0.5% in DMF). $R_f=0.45$ (solvent system chloroform:methanol (9:1), silica gel 60 ready-to-use plates $F_{254}$ (Merck), green colour with TDM reagent, grey-brown colour with iodine).

Figure 1:
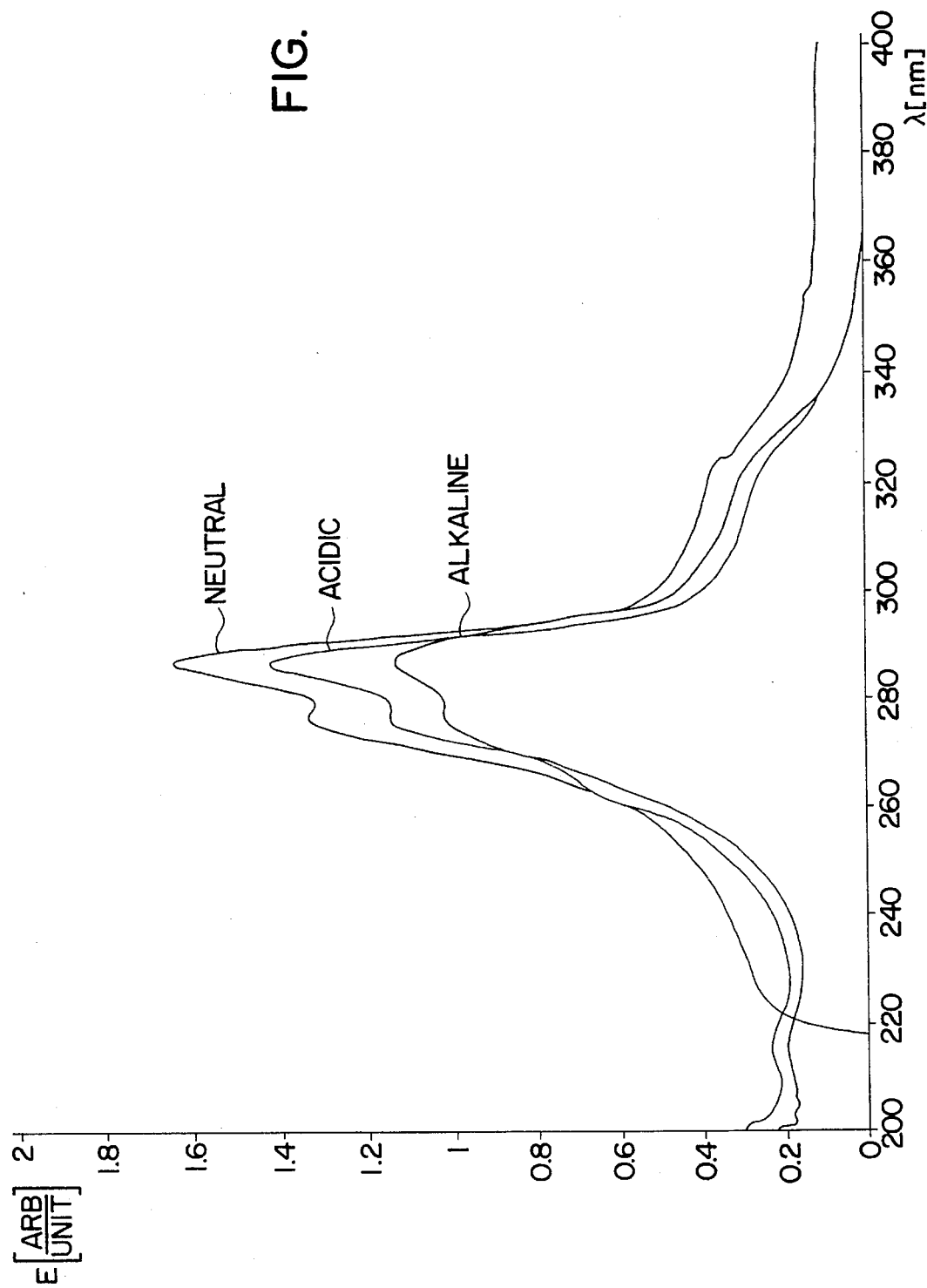

2) UV spectrum (FIG. 1, see annex)

Dissolution takes place in methanol (c=0.1 mg in 1 ml of $CH_3OH$). Acidic or alkaline pH is established by addition of 20 µl of 1N HCl or 1 N sodium hydroxide solution per ml of solution.

TABLE 2

Maxima [λ max.] and absorbances $\left[E\frac{1\%}{cm}\right]$ of the compound (Ia)

| | λmax [µm] | $\left[E\frac{1\%}{cm}\right]$ |
|---|---|---|
| neutral | 213.5 | 416 |
| | 276.0 | 2642 |
| | 285.0 | 3228 |
| acidic | 228 | 294 |
| | 275.5 | 2262 |
| | 285.5 | 2812 |
| alkaline | 215.5 | 368 |
| | 276.0 | 2300 |
| | 285.5 | 2834 |

Figure 2:
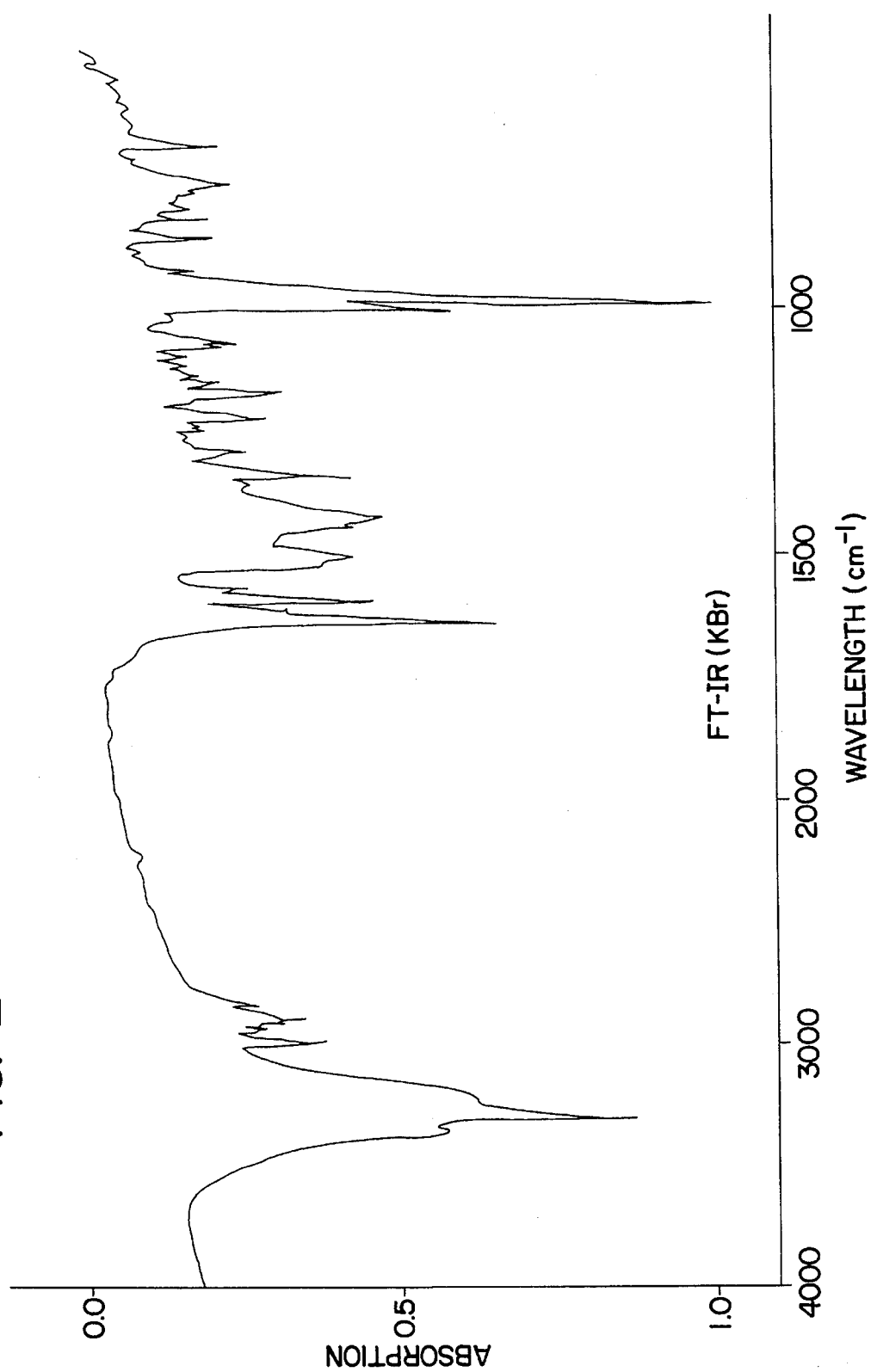

3) The IR absorption spectrum of the compound (Ia) is reproduced in FIG. 2 (abscissa: wavenumber in $cm^{-1}$; ordinate: absorption). If the substance is compressed in KBr discs, it shows absorption bands at the following wavenumbers (expressed in $cm^{-1}$):
Relative intensities:
vs=very strong
s=strong
m=medium
w=weak
sh=shoulder

TABLE 3

| Wavenumber in $cm^{-1}$ | Wavenumber in $cm^{-1}$ |
|---|---|
| 3400 (sh) | 1365 (m) |
| 330 (vs) | 1330 (w) |
| 3250 (sh) | 1280 (w) |
| 3020 (w) | 1220 (w) |
| 2945 (w) | 1120 (w) |
| 2855 (w) | 1030 (s) |
| 1655 (s) | 1000 (vs) |
| 1610 (m) | 875 (w) |
| 1600 (w) | 850 (w) |
| 1550 (sh) | 800 (w) |
| 1530 (m) | 725 (w) |
| 1445 (m) | |

Figure 3:
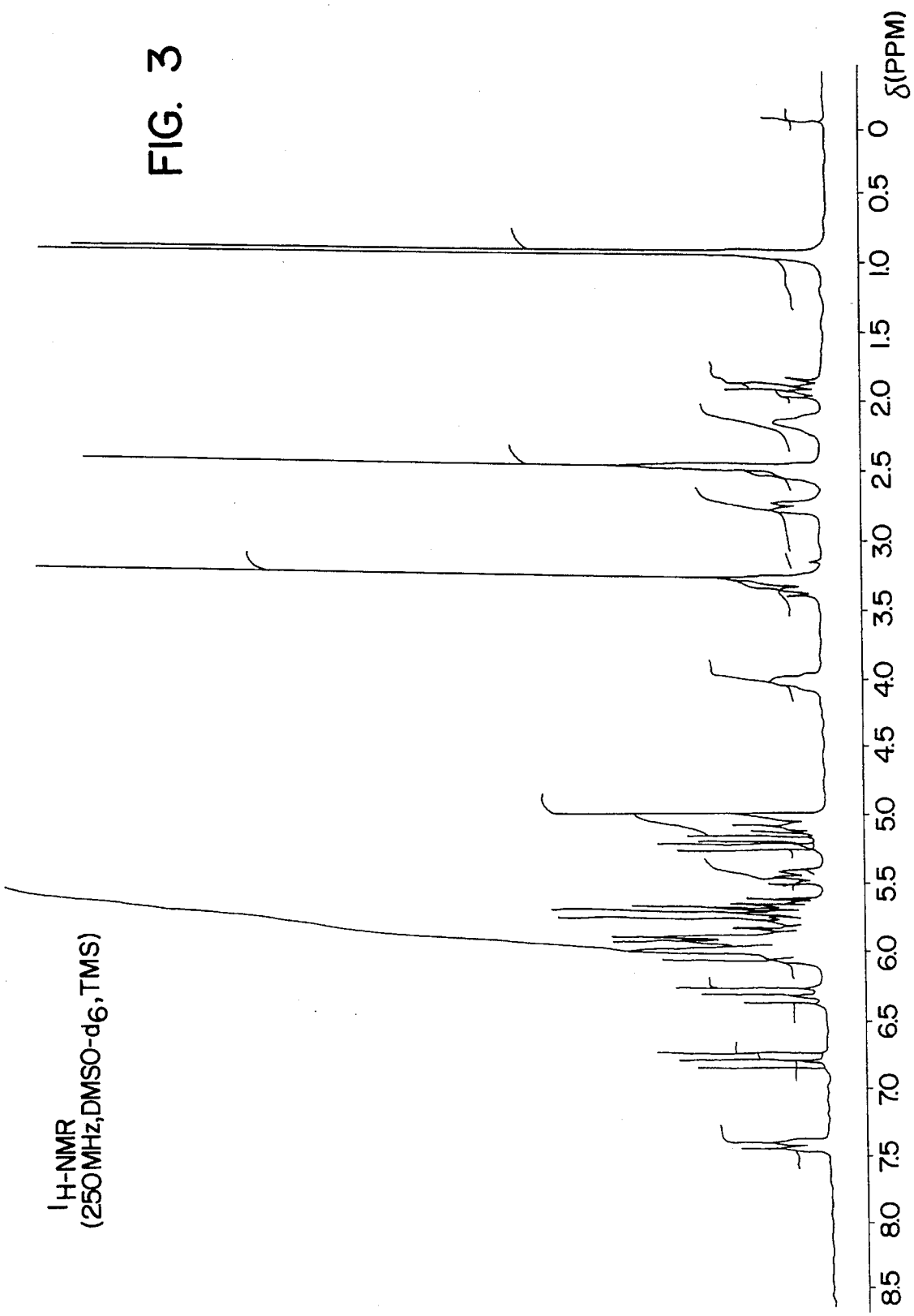

4) The $^1H$ nuclear magnetic resonance spectrum gives the signal position in parts per million (ppm) and vibrations per second as in FIG. 3. It was recorded in a dimethyl sulphoxide-$d_6$ solution of the compound with TMS as standard (internal) using a nuclear magnetic resonance spectrometer from Bruker at a field strength of 250 MHz.

By means of HIC heteroatom correlation spectroscopy, it was possible to assign to the carbon atoms the hydrogen atoms bonded to them:

TABLE 4

| Chem. shifts of the C atoms (ppm) | Assignment | H correlation (ppm) |
|---|---|---|
| 166.3 | CO—N< | — |
| 139.0 | CH= | 6.80 |
| 137.8 | CH= | 6.35 |
| 136.1 | CH= | 5.10 |
| 135.9 | CH= | 5.70 |
| 135.1 | CH= | 5.20 |
| 132.8 | CH= | 5.45 |
| 132.7 | CH= | 5.95 |
| 132.4 | CH= | 5.90 |
| 132.3 | CH= | 5.63 |
| 131.7 | CH= | 5.80 |
| 131.0 | CH= | 6.05 |
| 130.8 | CH= | 5.98 |
| 129.1 | CH= | 6.00 |
| 124.3 | CH= | 5.75 |
| 72.8 | CH<O | 4.1 |
| 44.3 | $CH_2$ | 3.4/2.85 |
| 42.0 | $CH_2$ | 2.65/1.95 |
| 40.7 | CH | 2.2 |
| 17.1 | $CH_3$ | 1.0 |

An OH group at δ = 5.0 ppm and an NH group at δ = 7.5 ppm were identified by H/D exchange The linkage of the C atoms to one another and thus the basic structure of the molecule can be ascertained by determination of the coupling of the corresponding hydrogen atoms bonded to them in the two-dimensional $^1H$, $^1H$-COSY NMR spectrum. To do this, the chemical shift of each H atom is determined in the 2D plot (see Table 4).

The coupling components are ascertained in the correlation diagram. As an example, the coupling components of the H atom at δ=4.1 ppm are identified in FIG. 3: an OH group at 5.0 ppm, an olefinic H at 5.2 ppm and two diastereotopic protons at δ=1.95 and 2.65 ppm.

Between 5.1 and 6.1 ppm are 12 protons, in some cases coupling to one another in a complicated manner. All signals can be arranged in a correlation diagram (Table 5):

TABLE 5

| δ of the H atom | Group | Signal multiplicity |
|---|---|---|
| 1.0 | $CH_3$ | d(d) |
| 1.95 | CH | dd |
| 2.2 | CH | sept(t) |
| 2.65 | CH | m |
| 2.85 | CH | dd |
| 3.40 | CH | dd |
| 4.1 | CH<O | ddd |
| 5.0 | OH | d |
| 7.5 | NH | dd |
| 5.1 | CH= | dd |
| 5.2 | CH= | dd |
| 5.45 | CH= | ddd |
| 5.63 | CH= | dd |
| 5.70 | CH= | m(dd) |
| 5.75 | CH= | m |
| 5.80 | CH= | dd |
| 5.85–6.10 | CH= 5x) | mm |
| 6.35 | CH= | dd |
| 6.80 | CH= | dd |

With the aid of a 600 MHz spectrum (Bruker, Karlsruhe), it was possible to assign all shifts. Accordingly, 3 double bonds with $J^3$ coupling constants of the protons between 14.5 Hz and 15.5 Hz have trans-configuration and one with a coupling constant of 11.5 Hz has cis-configuration.

6) The compound (Ia) shows a molecular peak at m/e=311 in mass spectroscopy under DCI conditions. The mass spectrum in the EI mode gives a high resolution of 311.1895 for the molecular peak (calculated for $C_{20}H_{25}NO_2$ 311.1885).

The other compounds according to the invention, which are included under the general formula (I), can be prepared by chemical derivatization of the natural substance cyclamenol of the general formula (Ia), these in turn then being a confirmation of its constitution.

In this process, the natural substance of the formula (Ia)

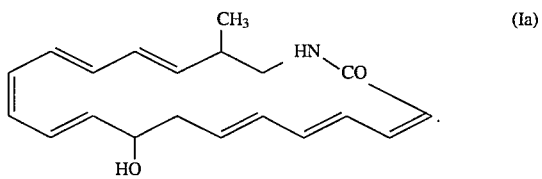

[A] in the case that $R^2$ (general formula I) represents acetyl, is reacted at room temperature with acetic anhydride in the presence of 4-(N,N-dimethylamino)pyridine under a protective gas atmosphere,

[B] in the case that $R^2$ (general formula I) represents the trimethylsilyl group, is reacted at room temperature with N,O-bis(trimethylsilyl)acetamide in the presence of pyridine and trimethylchlorosilane, likewise under a protective gas atmosphere, and

[C] in the case ($R^1$=H/$R^2$=H), $R^1$=H, $R^2$=OH), ($R^1+R^2$==O) and A—X in each case represent the —$CH_2$- group (general formula I), is hydrogenated at 0° C. with hydrogen in the presence of palladium on active carbon, in methanol.

The compounds of the general formulae (I) and (Ia) according to the invention can be employed as active compounds in medicaments for acute and chronic inflammatory processes and other pathological conditions in which white blood cells are involved. Their actions consist in the potent inhibition of the release of oxygen radicals, hydrolytically active enzymes such as, for example, β-glucuronidase and elastase and the oxidative myeloperoxidase from human polymorphonuclear neutrophils.

They are thus preferably suitable for the treatment and prevention of acute and chronic inflammations of the airways, such as allergies/asthma, bronchitis, rheumatism, arteriosclerosis, arthrosis, inflammations of the gastrointestinal tract, myocarditis and cardiac infarct.

Use Example

1. Isolation of the myeloperoxidase:

Myeloperoxidase from human polymorphonuclear neutrophils was used for the measurements. The latter were isolated from fresh venous whole blood according to the method of D. English and B. R. Andersen, Journal of Immunological Methods 5, (1974) 249–252.

$10^7$ cells were lysed at 0° C. for 10 min using 1 ml of 0.5% cetyltrimethylammonium bromide in 50 mmol/l sodium phosphate buffer pH 6.0, frozen and directly thawed again. This process was repeated twice. The suspension was then centrifuged at 40,000 g for 10 min. The supernatant was diluted with 50 mmol/l sodium phosphate buffer pH 6.0 according to its myeloperoxidase activity and used for the tests.

2. Test:

To carry out the tests, 10 μl of test sample are added to a dimethyl sulphoxide-containing solution (max. v/v 30%) with 30 μl of the myeloperoxidase solution prepared as described above=1–2.5 μg of protein, in a microtitre plate (Greiner) with a smooth bottom. The reaction is started by addition of a test mixture consisting of 250 μl of 50 mmol/l sodium phosphate buffer pH 6.0, 10 μl of $0.5 \times 10^{-3}$ mmol/l $H_2O_2$ and 10 μl of $2.5 \times 10^{-2}$ mol/l ortho-dianisidine in dimethyl sulphoxide. The increase in the absorbance is measured at 490 nm in an Elisa reader at 30° C. 6 measurements are carried out at an interval of 2 min and the increase in absorbance per minute is calculated. A control which instead of a test sample contains only the corresponding amount of dimethyl sulphoxide is prepared as the 100% value and then the inhibition by the sample is calculated. All measurements are carried out as a triplicate determination.

The compound (Ia) according to the invention of Example 1 causes an inhibition of the activity of the myeloperoxidase in the abovementioned test, as shown in Table 6:

TABLE 6

| Concentration of Example 1 μmol/l | % inhibition |
| --- | --- |
| 50 | 60 |
| 10 | 45 |
| 1 | 28 |
| 0.1 | 12 |

3. Leucocyte adhesion in small venules was investigated in the hamster cheek pouch (preparation according to Duling, MVR 5, 423–429, 1973). An increased adhesion is caused by the preparatory preparation of the cheek pouch. The substance reduces the leucocyte adhesion significantly from 0.1 mg/kg i.v. In further experiments, cheek pouches were superfused with $LTB_4$ for 10 min. The determination of the myeloperoxidase activity as a direct measure of the accumulation of neutrophilic leucocytes gives increases of around 80–100% compared to the control. At 1 mg/kg i.v., the new natural substance (1a/Example 1) prevents the rise in the MPO activity.

4. In vivo action of Example 1 (General Formula Ia)

Reduction of the infarct size in the rat infarct model

Method:

To determine the in vivo action of the compound from Example 1, a cardiac infarct was experimentally induced in anaesthetized (Trapanal i.p.) Wistar rats by ligation of the left coronary artery. After a 5-minute post-operative recovery phase, the compound from Example 1 in a dose of 1 mg/kg dissolved in 100% DMSO or solvents was infused for 6 min into the catheterized jugular vein of the ventilated rats and the coronary artery was occluded for 30 min. At the 25 minute point of the occlusion, the second administration of the compound from Example 1 or solvent is carried out under the conditions described above. After the end of the infusion and occulsion phase, the ligature was opened and the heart was reperfused for 90 min.

Determination of the infarct size:

For histological staining of the infarcted cardiac tissue, the heart was perfused ex vivo retrogressively with triphenyltetrazolium chloride (TTC, 1.5%) in 20 mM potassium phosphate buffer for 15 min and with 0.9% NaCl for 10 min at 37° C. and at a perfusion pressure of 100 mm Hg. The infarct sizes were calculated in percent by weight of infarcted to non-infarcted tissue and indicated in percent as average values and their standard deviations of 11 rats treated with the compound from Example 1 and of 11 treated with solvent.

Result:
The administration of 1 mg/kg each of the compound from Example 1 before occlusion and before reperfusion reduced the infarct size by 19.0±6.0% and 12.2±4.8%.

The present invention also includes pharmaceutical preparations which, in addition to inert, non-toxic, pharmaceutically suitable auxiliaries and excipients contain one or more compounds of the general formulae (I)/(Ia) or which consist of one or more active compounds of the formulae (I)/(Ia), and processes for the production of these preparations.

The active compounds of the formulae (I)/(Ia) should be present in these preparations in a concentration from 0.1 to 99.5% by weight, preferably from 0.5 to 95% by weight, of the total mixture.

In addition to the active compounds of the formulae (I)/(Ia), the pharmaceutical preparations can also contain other pharmaceutical active compounds.

The abovementioned pharmaceutical preparations can be prepared in a known manner by customary methods, for example with the excipient(s) or auxiliary(ies).

In general, it has proven advantageous to administer the active compound(s) of the formulae (I)/(Ia) in total amounts of about 0.01 to about 100 mg/kg, preferably in total amounts from about 1 mg/kg to 50 mg/kg, of body weight every 24 hours, if appropriate in the form of several individual doses, to achieve the desired result.

However, it may sometimes be advantageous to depart from the amounts mentioned, namely depending on the type and on the body weight of the subject to be treated, on individual behaviour towards the medicament, the nature and severity of the disorder, the type of preparation and administration, and the time or interval which administration takes place.

EXAMPLE 1

Cyclamenol (Ia)

EXAMPLE I

Preparation of the Inoculation Material for the Preculture 150 ml of sterile nutrient solution in a 1 l Erlenmeyer flask, of the following composition:

| | |
|---|---|
| Glucose | 4 g |
| Malt extract | 10 g |
| Yeast extract | 4 g |
| tap water pH 7.3 to 1000 ml | | are inoculated with mycelium of the Streptomyces strain MHW 846 and fermented at +28° C. on the rotary shaker at 240 rpm for three days. The washed cultures are used as inoculation material for further fermentation mixtures.

EXAMPLE II

Preparation of the Preculture for the Tank Fermentation 20 l of nutrient solution of the composition described in Example I and 20 ml of antifoam (SAG 5693, Union Carbide) are poured into a 30 l vessel having a stirrer, aeration and temperature control device and sterilized for 50 min at +121° C. After cooling of the nutrient solution to +28° C., it is inoculated with 300 ml of shaking cultures of the Streptomyces strain MHW 846 obtained as described in Example I, aerated with 10 l of sterile air per min (0.5 vvm) at 300 revolutions of the stirrer (blade stirrer) per minute and fermented at a temperature of +28° C. and an overlying pressure of 0.5 bar. After 2 days' fermentation, the contents are used as inoculation material for a batch in a 600 vessel.

EXAMPLE III

Fermentation in the 600 l Vessel 400 l of nutrient solution of the following composition:

| | |
|---|---|
| Glucose | 5 g |
| Dextrin | 40 g |
| Yeast autolysate | 1.5 g |
| Milk powder | 10 g |
| tap water to 1000 ml | | are sterilized at +121° C. for 60 min in a 600 l vessel adjusted to pH 7.0, cooled to +28° C. and inoculated with 20 l of the inoculation material obtained according to Example II. The fermentation of MHW 846 is carried out at +28° C., an aeration of 200 l of sterile air per min (0.5 vvm) and at an overlying pressure of 1 bar with 150 revolutions (blade stirrer) per minute. When after three to six days' fermentation the compound (1) according to the invention has been formed, the culture is harvested. Product formed: 1–2 mg/l.

EXAMPLE IV

The culture broth of a 400 l fermentation obtained according to Example III is separated in a Westphalia separator at pH 6.5–7.0 at 200–250 l/h.

The mycelium is treated with the same volume of methanol and stirred for 10 min. 30 l of ethyl acetate are then added and the mixture is stirred for a further 60 min. For phase separation, 10–15 l of water are added and the organic phase is separated. The organic phase is concentrated to about 5 l and directly further purified by means of chromatography. After separation of the mycelium, 400 l of supernatant are treated with 25 g of sodium chloride and extracted successively with 130 l and 30 l of ethyl acetate. The combined extracts are concentrated under reduced pressure to about 5 l.

EXAMPLE V

Further Concentration by Means of Medium Pressure Chromatography

Column: Glass column 10×18 cm
Flow rate: 20 ml/min
Detection: 280 nm
Stationary phase: Silica gel Si 60, 70–230 mesh
Eluent: Ethyl acetate p.a.

The crude extract from Example IV is further concentrated to an active compound content of about 1 mg/kg (according to analytical HPLC). The column eluate is collected in fractions and subjected to analytical high pressure liquid chromatography in accordance with the following parameters:
Solvent: 45% aqueous methanol LiChroSolv
Flow rate: 1 ml/min
Detection: 285 nm and 220 nm
Stationary phase: Chrompack 3×10 ODS 2
Fractions which contain the active compound are combined and the active compound is precipitated from concentrated solution using petroleum ether as an approximately 60–80% strength preparation and dried in vacuo.

EXAMPLE VI

Isolation of the Pure Substance

The pure substance is isolated from the concentrated product of Example IV by means of HPLC.
Column: Latek 5×25 cm ODS 2 5μ
Solvent: 55% aqueous methanol
Flow rate: 30 ml/min
Detection: 285 nm

EXAMPLES 2, 3 AND 4

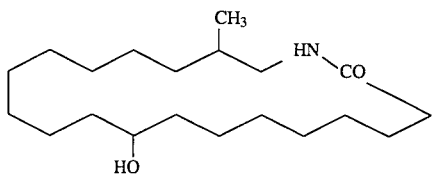
(2)

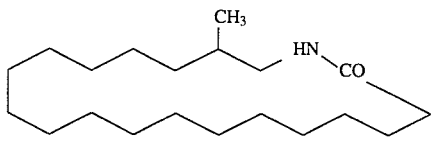
(3)

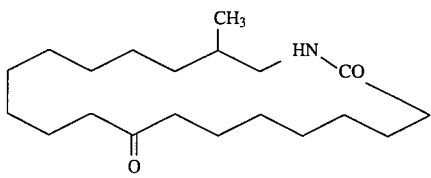
(4)

45 mg of the compound from Example 1 are dissolved in 10 ml of methanol at 0° C. and hydrogenated with hydrogen with stirring after addition of a spatula tipful of 10% strength palladium on active carbon. Hydrogenation is discontinued after 20 min, the mixture is filtered, and the filtrate is evaporated and purified by chromatography on silica gel 60. 20 mg of product of the compound of Example 2 which is homogeneous according to HPLC and $^1$H-NMR are obtained; $R_f$ (silica gel, CHCl$_3$/methanol 9:1) 0.47, grass-green colour with TDM reagent (becomes violet), UV-inactive, colourless crystals, m.p. 84° C. The $^{13}$C-NMR spectrum of the compound from Example 2 shows the complete hydrogenation of the double bond system. The highly resolved EI-MS shows the molecular peak at m/e= 325.2996 (calc. for C$_{20}$H$_{39}$NO$_2$: 325.2981). Elemental analysis has the following result:

|  | C | H | N |
|---|---|---|---|
| Calc.: (%) | 73.8 | 12.1 | 4.3 |
| Found: (%) | 73.9 | 10.7 | 4.3 |

FIG. 6 in the annex additionally shows the IR and $^1$H-NMR spectrum of the compound from Example 2.

In addition to the compound from Example 2, small amounts of the deoxygenation product of the compound from Example (3) and of the ketone of the compound from Example (4) additionally result.

EXAMPLE 5

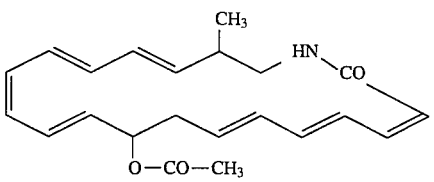

90 mg of the compound from Example 1 are dissolved in about 2 ml of pyridine under argon. 2 crystals of 4-(N,N-dimethylamino)pyridine (DMAP) and 40 drops of acetic anhydride are added and the mixture is stirred at RT for one hour. 220 ml of water are added and the mixture is extracted 5× using ethyl acetate. The organic phase is dried using sodium sulphate, concentrated and purified by chromatography on silica gel. 40 mg of product cyclamenol monoacetate which is homogeneous according to HPLC and $^1$H-NMR are obtained, $R_f$ (silica gel, chloroform/methanol 9:1) 0.84; green colour with TDM reagent, UV-active (254 nm), colourless crystals (needles), m.p. 260° C., FT-IR spectrum (KBr):

TABLE 8

| IR spectrum | |
|---|---|
| Wavenumber in cm$^{-1}$ | Wavenumber in cm$^{-1}$ |
| 3380 (sh) | 1535 (m) |
| 3295 (m) | 1445 (w) |
| 3005 (w) | 1365 (m) |
| 2950 (w) | 1240 (vs) |
| 2910 (w) | 1095 (w) |
| 2875 (w) | 1025 (m) |
| 1745 (vs) | 995 (vs) |
| 1650 (s) | 895 (w) |
| 1610 (m) | |

EXAMPLE 6

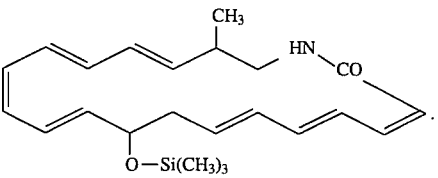

140 mg of the compound from Example 1 are dissolved in 5 ml of abs. acetonitrile. A solution of 500 mg of N,O-bis(trimethylsilyl)acetamide in a little acetonitrile, 0.3 ml of dry pyridine and 10 drops of trimethylchlorosilane are added at RT with stirring (argon). After 30 min, the mixture is evaporated at RT and dried at 0.1 mm Hg. The residue is purified by preparative thin layer chromatography on silica gel using dichloromethane/methanol 9:1 and 40 mg of colourless, amorphous solid cyclamenol(mono)trimethylsilyl ether are obtained, $R_f$ (silica gel, CHCl$_3$/methanol 9:1) 0.81, green colour with TDM reagent, UV-active, FT-IR (KBr):

TABLE 9

| IR spectrum | |
|---|---|
| Wavenumber in cm$^{-1}$ | Wavenumber in cm$^{-1}$ |
| 3395 (broad, vs) | 1390 (vs) |
| 2995 (m) | 1250 (s) |
| 2920 (sh) | 1100 (broad m) |
| 1720 (sh) | 1015 (m) |
| 1670 (broad, vs) | 890 (w) |
| 1550 (w) | 850 (s) |
| 1475 (w) | 775 (w) |

We claim:

1. A compound of the formula

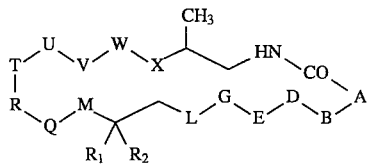

(I)

in which

A, B, D, E, G, L, M, Q, R, T, U, V, W and X in each case represent the >CH$_2$ group and R$^1$ and R$^2$ represent hydrogen or R$^1$ represents hydrogen and R$^2$ represents hydroxyl, or R$^1$ and R$^2$ together form the =O group, or A and B, D and E, G and L, M and Q, R and T, U and V and W and X in each case represent the —CH=CH— group, R$^1$ represents hydrogen and R$^2$ represents hydroxyl or represents the group of the formula —O—CO—CH$_3$ or O—Si(CH$_3$)$_3$.

2. A pharmaceutical composition which comprises an effective amount of a compound according to claim 1 and an excipient or auxiliary.

3. A method for treating acute or chronic inflammation which comprises administering to a host in need thereof an effective amount of a compound according to claim 1.

4. A process for preparing a compound according to claim 1 which comprises fermenting Streptomyces spec. MHW 846 or one of its mutants or variants under aerobic conditions in a nutrient medium which contains assimilable carbon and nitrogen sources and mineral salts followed by isolating the resulting compound.

* * * * *